US008755883B2

(12) United States Patent
Wariar et al.

(10) Patent No.: US 8,755,883 B2
(45) Date of Patent: Jun. 17, 2014

(54) TRACKING PROGRESSION OF CONGESTIVE HEART FAILURE VIA A FORCE-FREQUENCY RELATIONSHIP

(75) Inventors: Ramesh Wariar, Blaine, MN (US); Gerrard M. Carlson, Champlin, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 660 days.

(21) Appl. No.: 12/634,277

(22) Filed: Dec. 9, 2009

(65) Prior Publication Data

US 2010/0087890 A1  Apr. 8, 2010

Related U.S. Application Data

(63) Continuation of application No. 11/208,281, filed on Aug. 19, 2005, now Pat. No. 7,634,309.

(51) Int. Cl.
*A61N 1/365* (2006.01)
*A61B 5/025* (2006.01)

(52) U.S. Cl.
USPC ............................................ 607/17; 600/528

(58) Field of Classification Search
USPC ................. 600/485, 486, 513, 514, 528, 492; 607/6, 17, 23
See application file for complete search history.

(56) References Cited

U.S. PATENT DOCUMENTS

| | | | |
|---|---|---|---|
| 4,094,308 A | 6/1978 | Cormier | |
| 4,289,141 A | 9/1981 | Cormier | |
| 4,446,872 A | 5/1984 | Marsoner et al. | |
| 4,548,204 A | 10/1985 | Groch et al. | |
| 4,649,930 A | 3/1987 | Groch et al. | |
| 4,763,646 A | 8/1988 | Lekholm | |
| 4,905,706 A | 3/1990 | Duff et al. | |
| 4,915,113 A | 4/1990 | Holman | |
| 4,989,611 A | 2/1991 | Zanetti et al. | |
| 5,159,932 A | 11/1992 | Zanetti et al. | |
| 5,365,932 A | 11/1994 | Greenhut | |
| 5,496,361 A | 3/1996 | Moberg et al. | |
| 5,554,177 A | 9/1996 | Kieval et al. | |
| 5,674,256 A | 10/1997 | Carlson | |
| 5,685,317 A | 11/1997 | Sjostrom | |
| 5,687,738 A | 11/1997 | Shapiro et al. | |
| 5,697,375 A | 12/1997 | Hickey | |
| 5,700,283 A | 12/1997 | Salo | |
| 5,738,102 A | 4/1998 | Lemelson | |
| 5,792,195 A | 8/1998 | Carlson et al. | |

(Continued)

OTHER PUBLICATIONS

"U.S. Appl. No. 11/142,851, Final Office Action mailed Jul. 15, 2008", 7 pgs.
"U.S. Appl. No, 11/142,851, Final Office Action mailed Oct. 6, 2008", 7 pgs.
"U.S. Appl. No. 11/142,851, Non-Final Office Action mailed Feb. 7, 2008", 6 pgs.
"U.S. Appl. No. 11/142,851, Non-Final Office Action mailed May 21, 2008", 7 pgs.

(Continued)

*Primary Examiner* — Tammie K Heller
(74) *Attorney, Agent, or Firm* — Schwegman Lundberg & Woessner, P.A.

(57) ABSTRACT

A system, method, or device monitor a force-frequency relationship exhibited by a patient's heart. A contractility characteristic, such as a heart sound characteristic of an S1 heart sound, is measured. The contractility characteristic indicates the forcefulness of a contraction of the heart. The frequency at which the heart is contracting is determined. A group of (contractility characteristic, heart rate) pairs is stored in a memory device. The group of pairs defines a force-frequency relationship for the heart. The method may be implemented by an implantable device, or by a system including a implantable device.

29 Claims, 9 Drawing Sheets

(56) References Cited

U.S. PATENT DOCUMENTS

| | | |
|---|---|---|
| 5,836,987 A | 11/1998 | Baumann et al. |
| 5,853,005 A | 12/1998 | Scanlon |
| 5,991,661 A | 11/1999 | Park et al. |
| 6,026,324 A | 2/2000 | Carlson |
| 6,044,298 A | 3/2000 | Salo et al. |
| 6,044,299 A | 3/2000 | Nilsson |
| 6,045,513 A | 4/2000 | Stone et al. |
| 6,053,872 A | 4/2000 | Mohler |
| 6,058,329 A | 5/2000 | Salo et al. |
| 6,064,910 A | 5/2000 | Andersson et al. |
| 6,077,227 A | 6/2000 | Miesel |
| 6,152,884 A | 11/2000 | Bjorgaas |
| 6,264,611 B1 | 7/2001 | Ishikawa et al. |
| 6,298,269 B1 | 10/2001 | Sweeney |
| 6,312,378 B1 | 11/2001 | Bardy |
| 6,366,811 B1 | 4/2002 | Carlson |
| 6,368,283 B1 | 4/2002 | Xu et al. |
| 6,409,675 B1 | 6/2002 | Turcott |
| 6,415,033 B1 | 7/2002 | Halleck et al. |
| 6,440,078 B1 * | 8/2002 | Curiel et al. ............ 600/481 |
| 6,440,082 B1 | 8/2002 | Joo et al. |
| 6,477,406 B1 | 11/2002 | Turcott |
| 6,491,639 B1 | 12/2002 | Turcott |
| 6,527,729 B1 | 3/2003 | Turcott |
| 6,575,916 B2 | 6/2003 | Halleck et al. |
| 6,643,548 B1 | 11/2003 | Mai et al. |
| 6,650,940 B1 | 11/2003 | Zhu et al. |
| 6,665,564 B2 | 12/2003 | Lincoln et al. |
| 6,795,732 B2 | 9/2004 | Stadler et al. |
| 6,810,287 B2 | 10/2004 | Zhu et al. |
| 6,824,519 B2 | 11/2004 | Narimatsu et al. |
| 6,830,548 B2 | 12/2004 | Bonnet et al. |
| 6,839,593 B1 | 1/2005 | Sun et al. |
| 6,845,263 B2 | 1/2005 | Kawaguchi |
| 6,963,777 B2 | 11/2005 | Lincoln et al. |
| 7,039,462 B2 | 5/2006 | Pastore et al. |
| 7,052,466 B2 | 5/2006 | Scheiner et al. |
| 7,079,896 B1 | 7/2006 | Park et al. |
| 7,115,096 B2 | 10/2006 | Siejko et al. |
| 7,123,962 B2 | 10/2006 | Siejko et al. |
| 7,174,203 B2 | 2/2007 | Arand et al. |
| 7,634,309 B2 | 12/2009 | Wariar et al. |
| 2002/0001390 A1 | 1/2002 | Kawaguchi |
| 2002/0035337 A1 | 3/2002 | Oka |
| 2002/0082645 A1 | 6/2002 | Sweeney |
| 2002/0091332 A1 | 7/2002 | Bombardini |
| 2002/0107450 A1 | 8/2002 | Ogura |
| 2002/0147401 A1 | 10/2002 | Oka |
| 2002/0151812 A1 | 10/2002 | Scheiner et al. |
| 2002/0151938 A1 | 10/2002 | Corbucci |
| 2002/0188329 A1 | 12/2002 | Struble |
| 2003/0055352 A1 | 3/2003 | Hayek et al. |
| 2003/0055461 A1 | 3/2003 | Girouard et al. |
| 2003/0069608 A1 | 4/2003 | Sweeney |
| 2003/0072458 A1 | 4/2003 | Halleck et al. |
| 2003/0093002 A1 | 5/2003 | Kuo |
| 2003/0093003 A1 | 5/2003 | Watrous et al. |
| 2003/0120159 A1 | 6/2003 | Mohler |
| 2003/0176896 A1 | 9/2003 | Lincoln et al. |
| 2003/0208240 A1 | 11/2003 | Pastore et al. |
| 2003/0216620 A1 | 11/2003 | Jain et al. |
| 2003/0229289 A1 | 12/2003 | Mohler |
| 2004/0024423 A1 | 2/2004 | Lincoln et al. |
| 2004/0039419 A1 | 2/2004 | Stickney et al. |
| 2004/0039420 A1 | 2/2004 | Jayne et al. |
| 2004/0064056 A1 | 4/2004 | Ogura |
| 2004/0078059 A1 | 4/2004 | Ding et al. |
| 2004/0078060 A1 | 4/2004 | Ding et al. |
| 2004/0106874 A1 | 6/2004 | Eigler et al. |
| 2004/0106960 A1 | 6/2004 | Siejko et al. |
| 2004/0106961 A1 | 6/2004 | Siejko et al. |
| 2004/0127792 A1 | 7/2004 | Siejko et al. |
| 2004/0138572 A1 | 7/2004 | Thiagarajan |
| 2004/0167417 A1 | 8/2004 | Schulhauser et al. |
| 2004/0204744 A1 | 10/2004 | Penner et al. |
| 2004/0215264 A1 | 10/2004 | Van Bentem |
| 2004/0225332 A1 | 11/2004 | Gebhardt et al. |
| 2004/0230129 A1 | 11/2004 | Haefner |
| 2004/0236239 A1 | 11/2004 | Murray et al. |
| 2004/0254481 A1 | 12/2004 | Brodnick |
| 2004/0254483 A1 | 12/2004 | Zdeblick et al. |
| 2004/0267147 A1 | 12/2004 | Sullivan |
| 2004/0267148 A1 | 12/2004 | Arand et al. |
| 2005/0010257 A1 | 1/2005 | Lincoln et al. |
| 2005/0027323 A1 | 2/2005 | Mulligan et al. |
| 2005/0033190 A1 | 2/2005 | Bauer |
| 2005/0102001 A1 | 5/2005 | Maile et al. |
| 2005/0119708 A1 | 6/2005 | Haefner |
| 2006/0020294 A1 | 1/2006 | Brockway et al. |
| 2006/0122651 A1 | 6/2006 | Whitman |
| 2006/0167334 A1 | 7/2006 | Anstadt et al. |
| 2006/0247702 A1 * | 11/2006 | Stegemann et al. ............ 607/17 |
| 2006/0276849 A1 | 12/2006 | Carlson et al. |
| 2006/0282000 A1 | 12/2006 | Zhang et al. |
| 2007/0043299 A1 | 2/2007 | Wariar et al. |

OTHER PUBLICATIONS

"U.S. Appl. No. 11/142,851, Non-Final Office Action mailed Dec. 19, 2008", 6 pgs.

"U.S. Appl. No. 11/142,851, Notice of Allowance mailed Sep. 27, 2007", 9 pgs.

"U.S. Appl. No. 11/142,851, Notice of Allowance mailed Oct. 6, 2009", 6 pgs.

"U.S. Appl. No. 11/142,851, Response filed May 7, 2008 to Non-Final Office Action mailed Feb. 7, 2008", 8 pgs.

"U.S. Appl. No. 11/142,851, Response filed Jun. 23, 2009 to Non-Final Office Action mailed May 21, 2009", 15 pgs.

"U.S. Appl. No. 11/142,851, Response filed Aug. 16, 2007 to Non-Final Office Action mailed May 18, 2007", 17 pgs.

"U.S. Appl. No. 11/142,851, Response filed Mar. 2, 2009 to Non-Final Office Action mailed Dec. 19, 2008", 7 pgs.

"U.S. Appl. No. 11/208,281, Non-Final Office Action mailed Oct. 28, 2008", 13 pgs.

"U.S. Appl. No. 11/208,281, Response filed Mar. 3, 2008 to Restriction Requirement mailed Jan. 31, 2008", 11 pgs.

"U.S. Appl. No. 11/208,281, Response filed Aug. 14, 2008 to Final Office Action mailed May 14, 2008", 19 pgs.

"U.S. Appl. No. 11/208,281, Restriction Requirement mailed Jan. 31, 2008", 8 pgs.

"U.S. Appl. No. 11/208,281, Response filed Jan. 28, 2009 to Non-Final Office Action mailed Oct. 28, 2008", 13 pgs.

"U.S. Appl. No. 11/208,281, Response filed May 7, 2009 to Restriction Requirement mailed Apr. 16, 2009", 8 pgs.

"U.S. Appl. No. 11/208,281, Restriction Requirement mailed Apr. 16, 2009", 6 pgs.

"U.S. Appl. No. 11/208,281, Final Office Action mailed May 14, 2008", 10 pgs.

"U.S. Appl. No. 11/208,281, Non-Final Office Action mailed Aug. 10, 2007", 9 pgs.

"U.S. Appl. No. 11/208,281, Notice of Allowance mailed Aug. 4, 2009", 7 pgs.

"U.S. Appl. No. 11/208,281, Response filed Nov. 13, 2007 to Non-Final Office Action mailed Aug. 10, 2007", 44 pgs.

Jaski, B. E., "Chapter 3—Circulation, Part 1: The Problem of Heart Failure", *Basics of Heart Failure: A Problem Solving Approach*, Kluwer Academic Publishers, Norwell, MA, (2000), 25-52.

Little, W. C., et al., "Assessment of Normal and Abnormal Cardiac Function", *Heart Disease: A Textbook of Cardiovascular Medicine*, W.B. Saunders, Philadelphia PA, (2001), 479-502.

Wariar, R., et al., "Tracking Progression of Congestive Heart Failure Via a Force-Frequency Relationship", U.S. Appl. No. 11/208,281, filed Aug. 19, 2005, 41 pgs.

"U.S. Appl. No. 11/142,851, Non-Final Office Action mailed May 18, 2007", 7 pgs.

"U.S. Appl. No. 11/142,851, Non-Final Office Action mailed on Dec. 19, 2008", 7 pgs.

* cited by examiner

TRACKING PROGRESSION OF CONGESTIVE HEART FAILURE VIA A FORCE-FREQUENCY RELATIONSHIP

CROSS REFERENCE TO RELATED APPLICATION

This application is a continuation of U.S. application Ser. No. 11/208,281, filed Aug. 19, 2005, now U.S. Pat. No. 7,634,309, which is hereby incorporated by reference in its entirety.

TECHNICAL FIELD

This document relates to cardiac rhythm management devices that are arranged to detect contractility such as by using heart sounds, and more particularly to cardiac rhythm management devices that can monitor the progression of congestive heart failure by observing the force-frequency relationship exhibited by a patient's heart.

BACKGROUND

Congestive heart failure is a condition in which a heart is unable to circulate enough blood to satisfy the metabolic demands of the body's various tissues and organs. People suffering from congestive heart failure may experience shortness of breath and fatigue. Such people may also exhibit fluid retention, referred to as edema. It is estimated that more than twenty-two million people suffer from congestive heart failure.

There exist many underlying causes of congestive heart failure. For example, congestive heart failure may be caused by a past heart attack, narrowed coronary arteries that restrict the supply of blood to the heart, various heart valve diseases, or congenital heart defects, to name a few. Those suffering from congestive heart failure may exhibit an arrhythmia that exacerbates the patient's heart failure. For example, a patient may exhibit left bundle branch block, a condition in which transmission of an electrical signal to the left ventricle is delayed. Ordinarily, electrical pulses propagate through the heart, causing the various cardiac muscle cells to contract when excited by the pulses. Usually, the cycle of electrical excitation of the heart is initiated by the sinoatrial node. An electrical impulse is generated by the sinoatrial node, and propagates from the sinoatrial node to the right and left atria. For normal propagation of the electrical impulse, the right and left atria contract at substantially the same time. Contraction of the atria force blood from the right and left atria into the right and left ventricles, respectively. Eventually, the electrical impulse reaches the atrioventricular node. From the atrioventricular node, the electrical impulse is carried along right and left bundle branch fibers to a network of fast-conducting Purkinje fibers that extend throughout most of the endocardial surface of the ventricles. The ventricles, when excited by the electrical impulse, normally contract at substantially the same time, causing the blood therein to exit and travel to either the lungs or the peripheral arterial system. In a heart suffering from left bundle branch block, the contraction of the left ventricle is retarded relative to contraction of the right ventricle. This results in an uncoordinated and inefficient heart contraction. Other conduction abnormalities may results from congestive heart failure (e.g., right bundle branch block).

Recently, implantable devices similar to traditional pacemakers or cardioverters (with pacing functionality) have been developed to address the problem of asynchronous left and right chamber contraction in congestive heart failure patients. Typically, these devices deliver electrical impulses to both ventricles of the heart timed to ensure that they contract together, thereby rectifying the asynchrony. Other pacing schemes to resynchronize a heart's contraction also exist. Such resynchronization pacing schemes are referred to generally as "cardiac resynchronization therapy" (CRT). (Cardiac rhythm management devices employing CRT may be referred to as "CRT devices.") Accordingly, a growing number of patients suffering from congestive heart failure use implantable CRT devices.

SUMMARY

There is a need for CRT devices that monitor the progression of a patient's congestive heart failure. Otherwise, a transthoracic echocardiogram of the patient's heart is generally obtained—a costly and perhaps inconvenient procedure. If a CRT device tracks the progression of a patient's congestive heart failure, the patient's health care could be improved by providing the patient's physician with timely and cost-efficient information.

This document describes, among other things, an implantable device that monitors CHF progression. One example describes a method that includes measuring a contractility characteristic of a heart, such as by using a heart sound characteristic of an S1 heart sound indicating forcefulness of a contraction of a heart. The method also includes determining how frequently the heart is contracting. Finally, a set of (contractility characteristic, heart rate) pairs is stored in a memory device. The set of pairs defines a force-frequency relationship for the heart. In certain examples, this constitutes a set of (heart sound characteristic, heart rate) pairs.

In another example, a method includes receiving, at a first point in time, a first set of (contractility characteristic, heart rate) pairs defining a first force-frequency relationship for a patient's heart. The method also includes receiving, at a second point in time, a second set of (contractility characteristic, heart rate) pairs defining a second force-frequency relationship for the patient's heart. A trend between the first and second force-frequency relationships for the patient's heart is determined.

In yet another example, an implantable device includes a transducer that obtains contractility information, such as by converting heart sounds into an electrical signal. The device also includes a sense amplifier channel that detects depolarizations of a chamber of a heart, a memory device, and a control circuit that is coupled to the transducer, sense amplifier channel, and memory device. In certain examples, the control circuit receives the electrical signal, identifies an S1 heart sound, and converts the S1 heart sound into morphological data representing a forcefulness of a contraction of a heart. The control circuit also determines how frequently the heart is contracting. Further, the control circuit stores in the memory device a force-frequency relationship for the heart. The stored force-frequency relationship is based upon the frequency of contraction of the heart and also based upon the morphological data of the S1 heart sound.

In yet another example, a computing system includes an I/O interface, a memory device, and a control circuit coupled to the I/O interface and the memory device. The control circuit receives via the I/O interface first and second force-frequency relationships for a patient's heart, and determines or presents (e.g., via an output device) a trend between the first and second force-frequency relationships for the patient's heart.

In certain examples, as further described below, the present system or methods involve measuring a force-frequency response. The force-frequency response is typically measured using LV dP/dt plotted against heart rate (or pacing rate). Since the S1 heart sound is sensitive and proportional to changes in LVdP/dt, the force-frequency response can be measured as a function of S1 vs. heart rate. The force-frequency response feature could have applicability for not only CRT but also for the heart failure patient with an implantable cardioverter-defibrillator.

DETAILED DESCRIPTION

Increasing heart rate typically increases the contractile force generated by healthy heart muscle. This phenomenon is called the force-frequency response and is thought to be a result of the incomplete removal of calcium ions that enter the heart muscle cells during each electrical stimulus (action potential) that precedes every heart beat. Normal force-frequency response is dependent on the proper functioning of complex calcium handling processes in heart muscle—heart failure typically results in impaired calcium handling, which in turn affects the force-frequency response. In normal heart muscle strips, maximal force is typically achieved at rates of about 120-150 beats/minute. In contrast, in an isolated heart muscle with cardiomyopathy, an increase in heart rate is typically accompanied by a decrease in twitch force, and in severely diseased hearts, by an increase in diastolic tension. Thus, the progression of congestive heart failure may be monitored by observing a deterioration of the force-frequency response of cardiac muscle.

Figure 1:
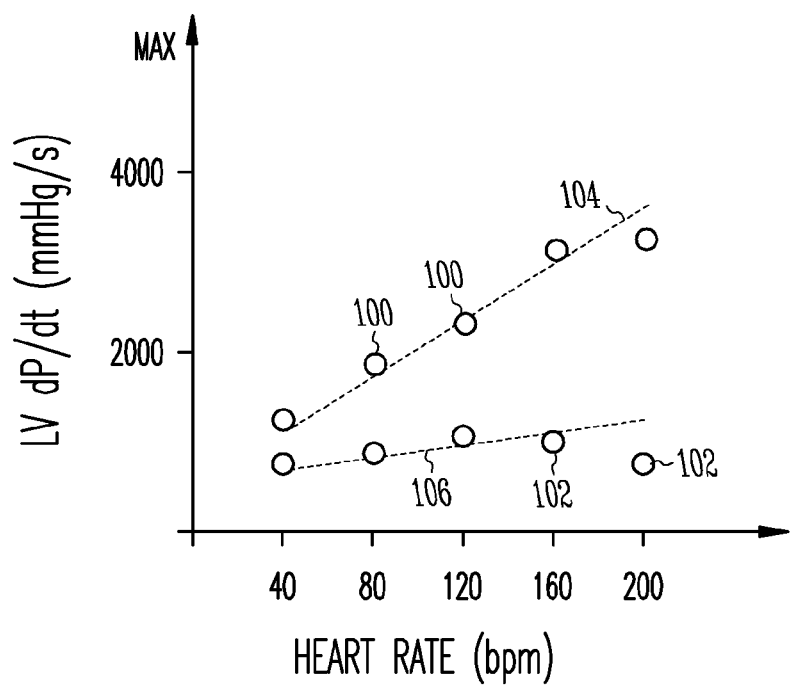
FIG. 1 depicts exemplary force-frequency relationships.

The force-frequency relationship measured in-vivo is illustrated in FIG. 1. FIG. 1 depicts a Cartesian plane, with maximum left ventricular rate of pressure change (a quantity that corresponds to the forcefulness of a cardiac contraction) measured along the y-axis, and heart rate measured along the x-axis. The data points presented in FIG. 1 are merely conceptual, and illustrate certain relevant principles.

In FIG. 1 depicts a first force-frequency relationship 100 (also referred to herein as a "force-frequency curve" or a "curve"). The terms "force-frequency relationship," "force frequency curve," and "curve" refer to the set of (x,y) pairs relating heart rate and forcefulness of contraction (as exhibited by maximum left ventricular rate of pressure change), as opposed to the dotted line approximately joining the pairs (the dotted line is discussed below). The first curve 100 conceptually illustrates the force-frequency response, as would typically be observed in a healthy human being. The curve 100 is monotonic and increasing. As the healthy patient's heart beats faster, the forcefulness of each contraction increases.

Congestive heart failure patients typically exhibit a deterioration of the force-frequency response. Conceptualized force-frequency relationship 102 of a patient suffering from congestive heart failure is also depicted in FIG. 1. As can be seen from the force-frequency curve 102, for a given elevation in heart rate, a heart with CHF typically does not exhibit as drastic of an increase in forcefulness of contraction as exhibited by a healthy heart. Therefore, by tracking the deterioration of the force-frequency response, the progression of congestive heart failure may be observed.

One way in which the deterioration of the force-frequency response may be observed is to consider each curve 100 and 102 as approximately exhibiting a slope. To that end, a linear regression may be performed upon the data points defining a curve 100, and 102, thereby generating an equation for a line 104 or 106 defining a "best fit" to the data points. FIG. 1 depicts a linear regression 104 of the first curve 100 and a linear regression 106 of the second curve 102. By inspection, one can see that the slope of the first regression 104 is greater than the slope of the second regression 106. For a given patient, as congestive heart failure worsens, it is expected that the slope of the line fit to the patient's force-frequency curve will diminish. Therefore, progression of congestive heart failure may be tracked and quantified by keeping track of the slope of the linear regression of a patient's force-frequency curve over time. Alternatively curvilinear functions can be fitted to the data points and similar information about slopes can be extracted.

The CHF curve 106 departs from substantial linearity somewhere between 120 and 160 beats per minute (at which point the curve departs so significantly that it even exhibits a negative slope in this conceptual example). The healthy heart curve 104 departs from substantial linearity at about 200 beats per minute, for example. For a given patient, as congestive heart failure worsens, it is expected that the particular heart rate at which the patient's force-frequency relationship departs from substantial linearity will decrease. Therefore, progression of congestive heart failure may be tracked and quantified by keeping track over time of the heart rate at which the patient's force-frequency relationship departs from substantial linearity.

To recap, a cardiac rhythm management device may track the progression of congestive heart failure in a given patient by determining and storing the force-frequency relationship exhibited by the patient's heart over time. This typically involves relating the force of contraction to the heart rate (frequency of depolarizations). The forcefulness of the heart's contraction may be indicated by the maximum left ventricular rate of pressure change. This is not easily directly measured. However, median (or other central tendency of) peak-to-peak amplitude of a group of S1 heart sounds is a good indicator of the maximum left ventricular rate of pressure change.

The heart makes certain sounds as it progresses through a cardiac cycle, which includes contraction of the atria, followed by contraction of the ventricle, and the expansion of the atria and ventricles to allow re-filling with blood. The heart sounds are caused by changes in circulation of the blood through the heart brought about by opening and closing of various heart valves. These heart sounds occur in a characteristic sequence, and are respectively referred to as S1, S2, S3 and S4.

The S1 heart sound is caused by acceleration and deceleration of blood, and closure of the mitral and tricuspid valves. The S1 heart sound generated during a given cardiac cycle exhibits heart sound characteristics (e.g., median peak-to-peak amplitude of a set of S1 heart sounds) that are indicative of the maximum rate of change of pressure in the left ventricle during the given cardiac cycle. In turn, the maximum rate of change of pressure in the left ventricle (e.g., LVdP/dt) is indicative of left ventricular contractility, which indicates the forcefulness of a heart's contraction. LVdP/dt is sensitive to contractility when it is measured during the isovolumic period, i.e., the period where cardiac muscle is contracting and the ventricular chamber valves (aortic and mitral valves) are closed.

As a result of the Frank-Starling mechanism LVdP/dt is also sensitive to the preload applied to heart chamber when it fills with blood. Preload may be measured directly or indirectly from several parameters such as LV end diastolic volume, LV end diastolic pressure, pulmonary capillary wedge pressure, pulmonary artery pressure, or S3 amplitude (which can be correlated with filling pressure). Typically LVdP/dt is divided by the end diastolic pressure to correct for preload related changes in dP/dt to obtain something that more closely represents contractility independent of preload effects. Similarly, when used as a surrogate for dP/dt the measured S1 amplitude can be adjusted to reduce preload-related effects using such metrics, thus making it a more accurate contractility index.

There is an approximate linear relationship between the median or average peak-to-peak amplitude of a group of S1 heart sounds and the median or average maximum rate of change of pressure in the left ventricle during the cardiac cycles from which the heart sounds were detected. Therefore, the median peak-to-peak amplitude exhibited by a group of S1 heart sounds may be used as a surrogate for the maximum left ventricular rate of pressure change.

Figure 2:
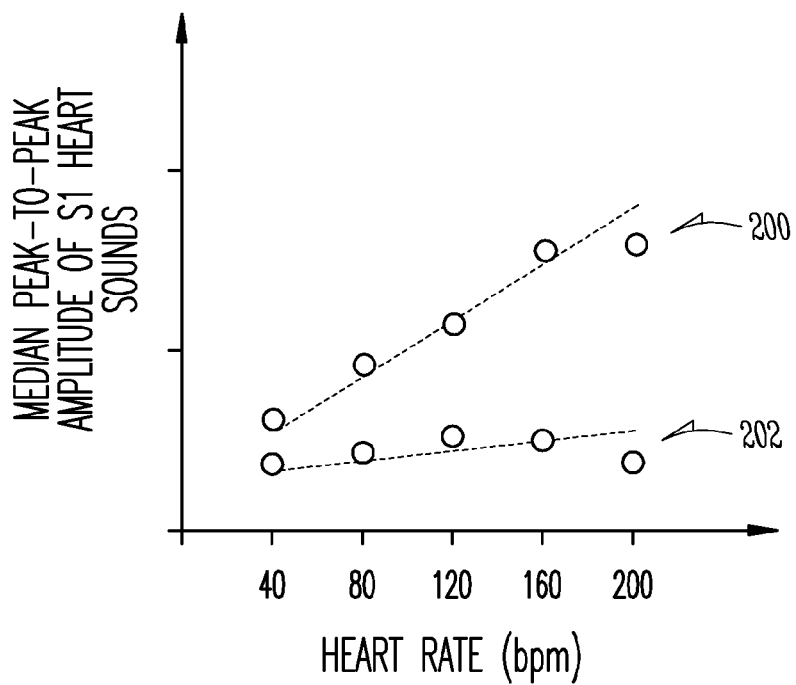
FIG. 2 depicts peak-to-peak amplitude of S1 heart sounds versus the heart rate.

Because of this relationship between the S1 heart sound and maximum rate of change of left ventricular pressure, a patient's force-frequency relationship may be expressed using an x-y chart having median peak-to-peak amplitude of a set of heart sounds measured along its y-axis, and the heart rate along the x-axis. Such an exemplary conceptualized chart is shown in FIG. 2. The curves 200 and 202 relating to a healthy (200) and CHF heart (202), respectively, exhibit similar characteristics as described with reference to FIG. 1.

Consequently, the terms "force-frequency relationship," "force frequency curve," and "curve" refer to the set of (x,y) pairs shown in FIG. 2, as well as the x,y pairs shown in FIG. 1, because the pairs in FIGS. 1 and 2 both relate heart rate and forcefulness of contraction. A scheme by which S1 heart sounds may be detected and measured is disclosed in U.S. patent application Ser. No. 11/142,851, entitled "SENSING RATE OF CHANGE OF PRESSURE IN THE LEFT VENTRICLE WITH AN IMPLANTED DEVICE," filed on Jun. 1, 2005, which is hereby incorporated by reference for all it teaches. For convenience, a method by which the median peak-to-peak amplitude of a set of S1 heart sounds may be determined is presented with reference to FIG. 3. Of course, other methods may be employed to find such a median, and other measures of central tendency may used. Further, other characteristics of the S1 heart sound may be used to reveal forcefulness of the contraction of the heart, including frequency content, energy content, energy content versus frequency, etc. As another example, forcefulness may be derived from time durations between S1 heart sounds (e.g., isovolumic contraction time) and electrocardiogram/electrogram (electrical) markers.

Figure 3:
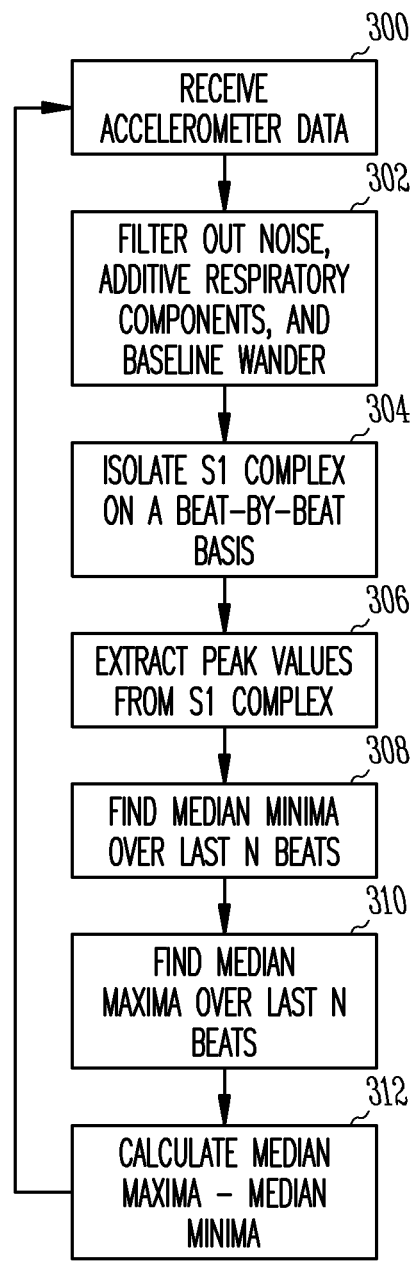
FIG. 3 depicts an exemplary scheme for determining peak-to-peak amplitude of an S1 heart sound.

The example method of FIG. 3 begins with the reception of raw accelerometer data at 300. At 302, the raw accelerometer data is conditioned, for example, to remove noise, respiratory components, and baseline wander. The resulting data stream substantially represents the heart sounds emitted by the heart.

This conditioned signal is then processed so as to isolate the S1 complex at 304. After isolation of the S1 complex at 304, peak values are extracted at 306. The peak-to-peak value is calculated by subtracting the minima from the maxima. The combined result of operations 300-306 is that, for each cardiac cycle, the peak-to-peak values exhibited by an S1 heart sound are extracted and stored in a manner to preserve their relationship to the cardiac cycle from which they were extracted. The median value of the peak-to-peak amplitudes are determined and stored along with its relationship to the cardiac cycle. Depending on the signal-to-noise ratio, this measurement can also be applied to cardiac cycles that have been ensemble averaged.

Figure 4:
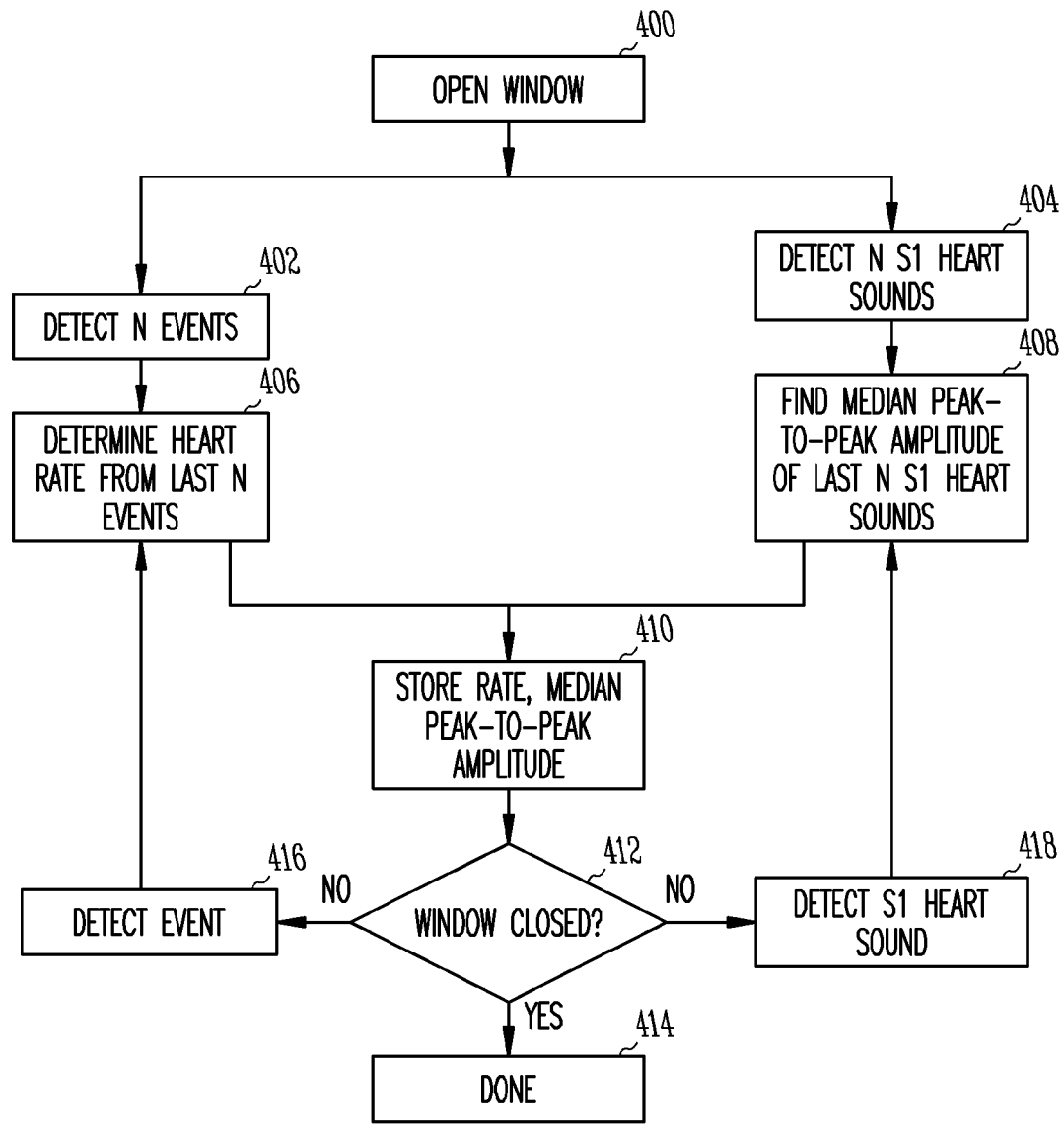
FIG. 4 depicts a method by which a force-frequency relationship may be obtained for a given patient.

FIG. 4 depicts a method by which a force-frequency relationship may be obtained for a given patient. The method of FIG. 4 may be executed by a cardiac rhythm management device. An example of such an implantable device is presented with reference to FIG. 10.

The method of FIG. 4 begins with the opening of a measurement window, as shown at 400. A measurement window is a span of time over which a patient's heart rate and heart sounds (or cardiac vibrations) is observed, in order to determine and store a force-frequency relationship.

After opening the window at 400 a set of N cardiac events (i.e., depolarizations) are detected at 402, and a set of N S1 heart sounds are measured at 404. The sets of N events and N heart sounds are measured/detected from the same set of cardiac cycles. Thereafter, the heart rate exhibited by the N events is determined at 406, and the median peak-to-peak amplitude exhibited by the N S1 heart sounds is determined at 408. For example, the heart rate may be found from the reciprocal of the R-R interval measured from the ECG. In an ensemble the average or median heart rate may be calculated. Operations 404 and 408 may be performed as described with reference to FIG. 3 or otherwise.

The heart rate determined at 406 and the median peak-to-peak amplitude determined at 408 make up an (x,y) pair described with reference to FIG. 2. After performing operations 406 and 408, the heart rate determined at 406 and the median peak-to-peak amplitude determined at 408 are stored at 410, so that their relationship or correspondence to each other is preserved. They may be stored as members of a paired or like data structure, for example.

After storing the (x,y) pair, it is determined at 412 whether the measurement window has closed. This determination may be made, for example, by having initialized a timer at 400, and determining at 412 whether the timer has elapsed. If the measurement window has closed, the method concludes at 414, and the force-frequency relationship is time or date stamped (or both) so that it can be associated with the time at which it was measured. If the window has not closed at 412, then control is passed to operations 416 and 418, whereupon another cardiac event is detected at 416, and another S1 heart sound is measured at 418.

After performing of operations 416 and 418, control is passed to 406 and 408, and the heart rate exhibited by the last N cardiac events is re-calculated in light of the newly detected cardiac event, and the median peak-to-peak amplitude exhibited by the last N S1 heart sounds is updated in light of the last measured S1 heart sound. Thus, operations 406, 408, 410, 412, 416, and 418 define a loop wherein a new (x,y) pair is determined and stored for each detected cardiac cycle, until the closing of the measurement window.

The method of FIG. 4 may be performed at intervals. For example, a cardiac rhythm management device may elect to open a measurement window once per month (or week, or every other week, etc.), in order to develop a set of (x,y) pairs defining a force-frequency relationship for a given patient. In one such scheme, the cardiac rhythm management device may use the ordinary physical activity of the patient to generate the various heart rates (over the span of a measurement window, a patient may go from rest, to ordinary activity, to exertion, such as climbing stairs).

As discussed below, the method of FIG. 4 may be modified in a variety of ways, such as to allow for normalization. Similar modifications may be made to the method described with reference to FIG. 5, discussed next.

Figure 5:
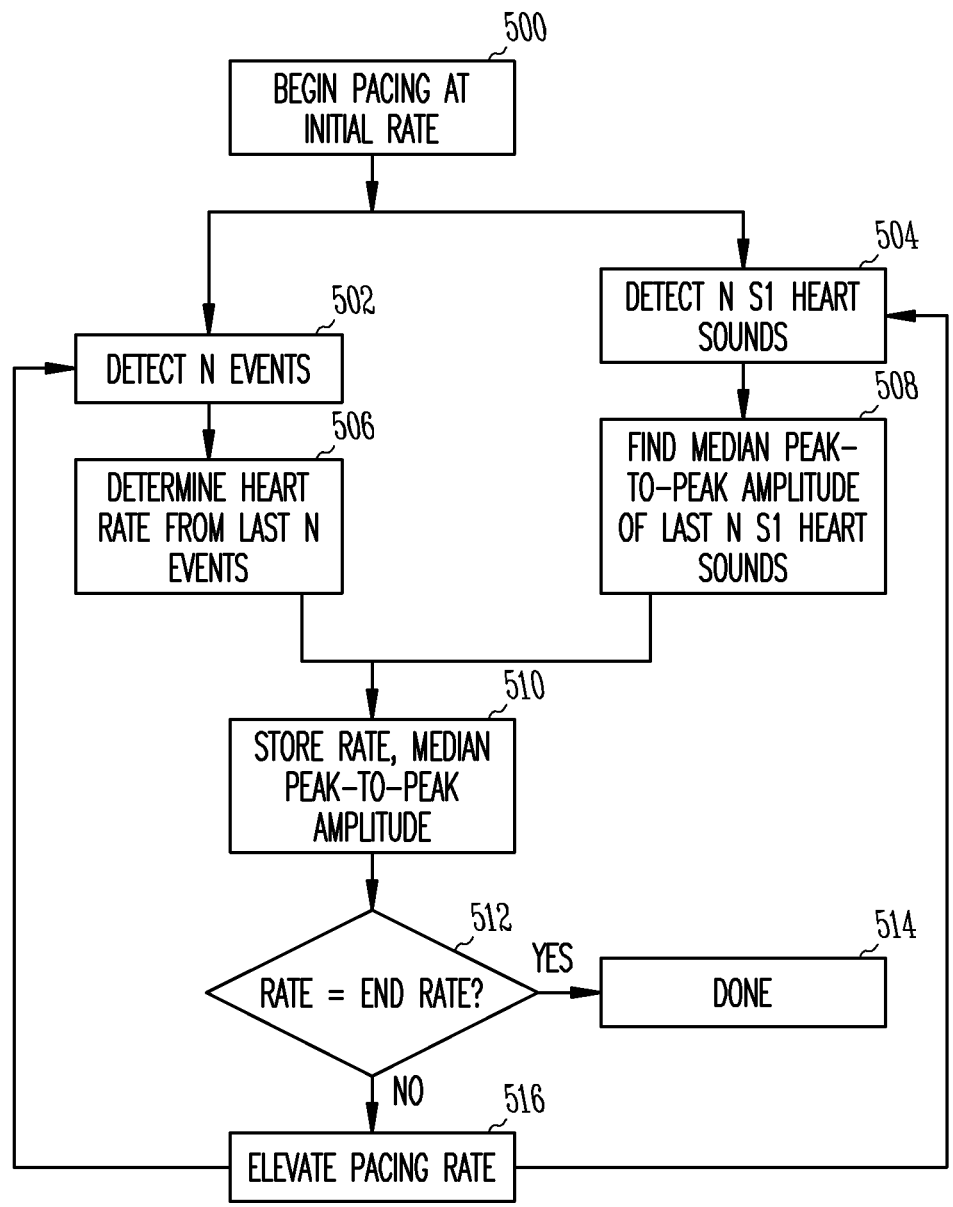
FIG. 5 depicts another method by which a force-frequency relationship may be obtained for a given patient.

FIG. 5 depicts another method by which a force-frequency relationship may be obtained for a given patient. The method of FIG. 5 (like the method of FIG. 4) may be executed by a cardiac rhythm management device. Again, an example of such a device is presented with reference to FIG. 10.

The method of FIG. 5 begins at 500 with pacing the patient at an initial pacing rate, which defines the lower end of the force-frequency relationship for the patient. A set of N cardiac events are then detected at 502, and a set of N S1 heart sounds are measured at 504. The group of N events and corresponding N heart sounds are measured/detected from the same set of cardiac cycles. At 506, the heart rate exhibited by the N events is determined. At 508, the median peak-to-peak amplitude exhibited by the N S1 heart sounds is determined. Operations 504 and 508 may be performed as described for FIG. 3 or otherwise.

The heart rate determined at 506 and the median peak-to-peak amplitude determined at 508 make up an (x,y) pair as described for FIG. 2. The heart rate determined in operation 506 and the median peak-to-peak amplitude determined in operation 508 are stored at 510, so that their correspondence to one another is preserved. They may be stored as members of a paired or like data structure, for example.

After storing the (x,y) pair, it is determined at 512 whether the rate at which the heart is being paced is equal to or greater than the upper end of the force-frequency relationship to be acquired. If so, the method ends at 514, and the force-frequency relationship is time and/or date stamped so that it can be associated with the time at which it was measured. If not, control passes to operation 516, and the pacing rate is elevated. For example, the pacing rate may be elevated by 5, 10, or 20 beats per minute each time operation 516 is executed. Thereafter, control is returned to operations 502 and 504. Another set of N cardiac cycles is detected/measured to determine the heart rate exhibited during the set of N cardiac cycles, and to determine the median peak-to-peak amplitude exhibited by that set of cardiac cycles. Thus, operations 502, 504, 506, 508, 510, 512, and 516 define a loop wherein a new (x,y) pair is determined and stored for each of a set of N detected cardiac cycles, at a given pacing rate.

Optionally, the method of FIG. 5 may be altered to exclude operations 502 and 506. Per such a modification, the heart rate is assumed to be the pacing rate, meaning that the (x,y) pair stored at 510 is based on the pacing rate and the measured median peak-to-peak amplitude exhibited by the set of N S1 heart sounds.

Optionally, the method of FIG. 5 may be performed so that operations 502-512 occur only twice: (1) a first (x,y) pair is determined and stored to define the lower end of the force-frequency relationship; and (2) a second (x,y) pair is determined and stored to define the upper end of the force-frequency relationship. Therefore, such a force-frequency relationship is defined by only two (x,y) pairs, resulting in a savings in computational complexity and measurement time.

The methods of FIGS. 4 and 5 may also be altered in other ways. For example, the methods of FIGS. 4 and 5 may be altered to include the following additional steps. In addition to measuring an S1 heart sound in a given cardiac cycle (operations 404, 418, and 504), all of the heart sounds in a given cardiac cycle may be measured. Then, before storing the (x,y) pair (at 410 and 510), the median peak-to-peak amplitude of the last N S1 heart sounds may be divided by the average (or median or other measure of central tendency) energy exhibited by the heart sounds in the last N cardiac cycles, so as to normalize the measurement. In other examples, the energy contained in an S1 heart sound may be divided by the energy contained in all heart sounds in a cardiac cycle in which the S1 heart sound is situated.

Alternatively, the methods of FIGS. 4 and 5 may be altered to achieve normalization in another way. For example, in addition to measuring an S1 heart sound in a given cardiac cycle (operations 404, 418, and 504), pulmonary artery pressure may be measured directly or indirectly (as with a implanted or external pressure sensor) and the timing between the pressure measurement and the cardiac cycle or ensemble is preserved. Before storing the (x,y) pair (operations 410 and 510), the median peak-to-peak amplitude of the last N S1 heart sounds may be divided by the average (or median or other measure of central tendency) pulmonary artery pressure exhibited during the last N cardiac cycles/ ensembles.

After performing the methods of FIG. 4 or 5 (or any of the variations thereof), the force-frequency relationships determined thereby may be transmitted to an external device, such as a computer, a programmer, a personal digital assistant, a cellular telephone, etc. An example of an external device is presented and discussed with respect to FIG. 10. Such an external device may store the force-frequency relationship (including its time/date stamp) in a manner that it is associated with a given patient. In one example, the external device presents a trend exhibited by the force-frequency relationships over time. To present such trend information, the methods described with reference to FIG. 6A, 6B, 7A, 7B, 8A, or 8B may be performed.

Figure 6A:
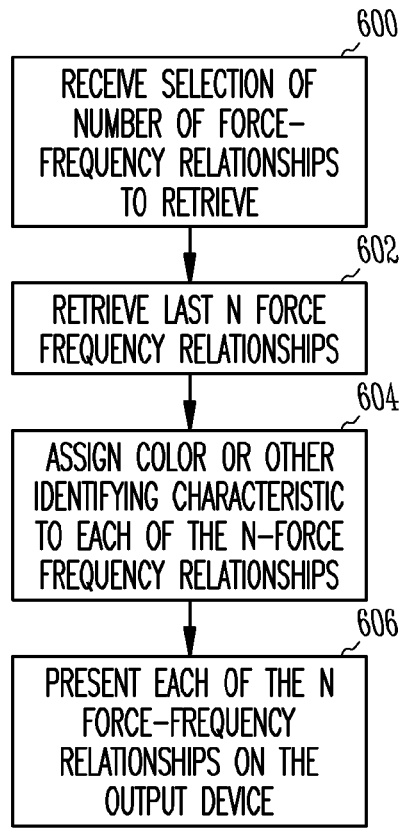
FIG. 6A depicts a method of presenting trend information.

FIG. 6A depicts a method of presenting trend information. The method of FIG. 6A begins at 600 in which the external device receives a selection (made, for instance, by a health care professional) of the number of force-frequency relationships to retrieve. At 602, that particular quantity of force-frequency relationships are retrieved from the data store in which they are housed. The corresponding time/date stamp information is retrieved at the same time, so that the date/time associated with each force-frequency relationship is known.

Figure 6B:
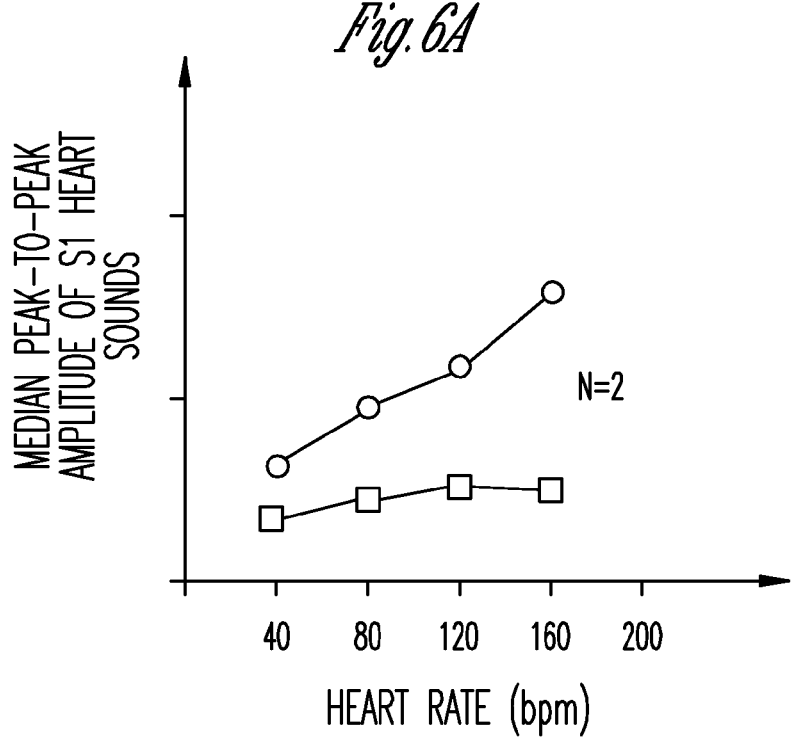
FIG. 6B depicts an exemplary appearance of the trend information of FIG. 6A.

Each of the retrieved force-frequency relationships is to be presented (e.g., displayed) via the external device's output device. So that the force-frequency relationships can be distinguished from one another, in one example, a unique characteristic is assigned to each one at 604. For example, a first force-frequency relationship might be presented in red, while a second is presented in blue, or a square may be used to represent an (x,y) pair in a first force-frequency relationship, while a circle is used for a second force-frequency, etc. Finally, at 606, each of the force-frequency relationships is presented. FIG. 6B presents an example of how such a presentation may appear, assuming that two force-frequency relationships were retrieved at 600.

Figure 7A:
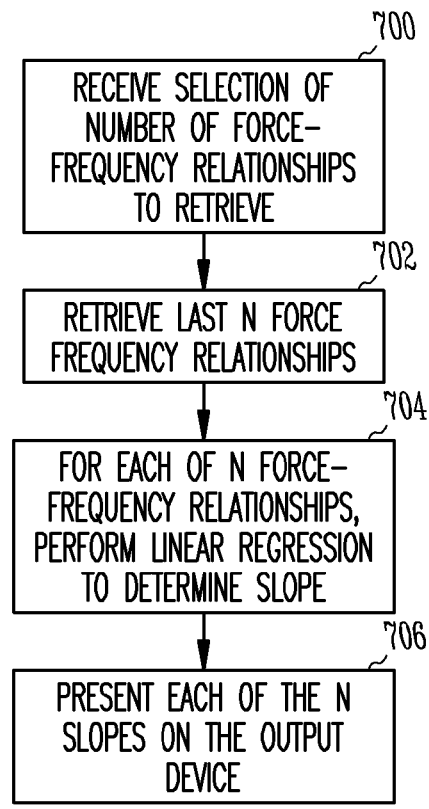
FIG. 7A depicts another method of presenting trend information.

FIG. 7A depicts another method of presenting trend information. Like the method of FIG. 6A, the method of FIG. 7A begins at 700 in which the external device receives a selection of the number of force-frequency relationships to retrieve. At 702, that particular quantity of force-frequency relationships is retrieved from the data store in which they are housed. As previously described, the corresponding time/date stamp information is retrieved at the same time, so that the date/time associated with each force-frequency relationship is known.

Figure 7B:
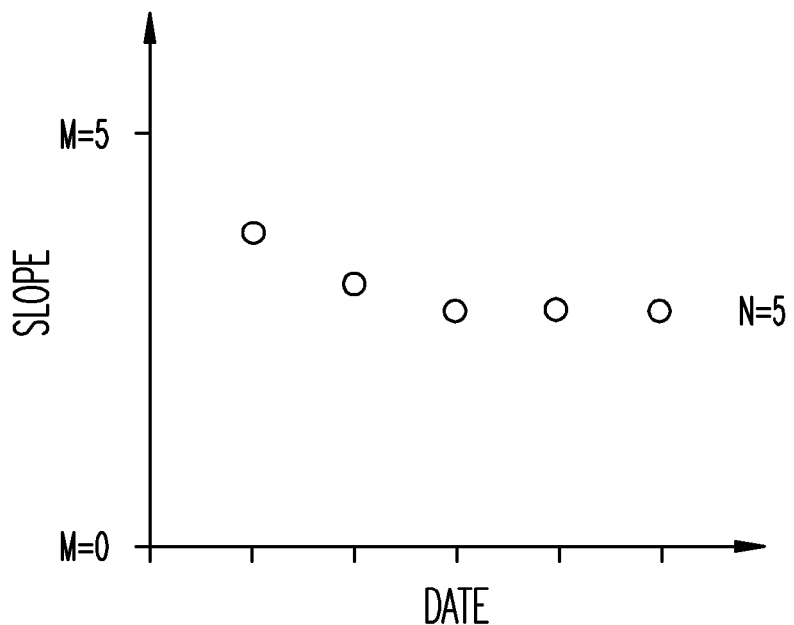
FIG. 7B depicts an exemplary appearance of the trend information of FIG. 7A.

Next, a linear regression and/or a curve fit is performed upon each of the retrieved force-frequency relationships, so that the slope for each such relationship may be determined at 704. Optionally, the linear regression may be performed on only a subset of the (x,y) pairs making up each force-frequency relationship. Finally, at 706, each slope calculated at 704 is presented (e.g., displayed), such as via the external device's output device. For example, the slopes may be presented on a x-y chart, with slope measured along the y-axis, and date/time measured along the x-axis. FIG. 7B presents an example of how such a presentation may appear, assuming that five force-frequency relationships were retrieved during the execution of operation 700. (Worsening of congestive heart failure is indicated by a decline in the slopes exhibited by successive the force-frequency relationships, as shown in FIG. 8B).

Figure 8A:
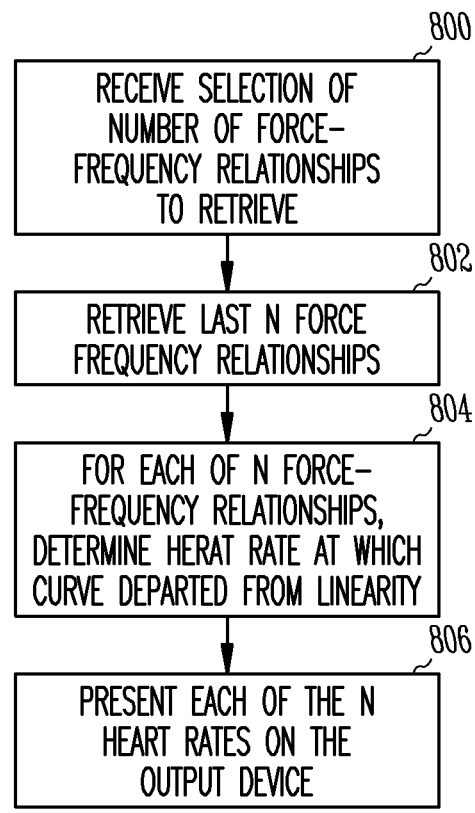
FIG. 8A depicts yet another method of presenting trend information.
Figure 8B:
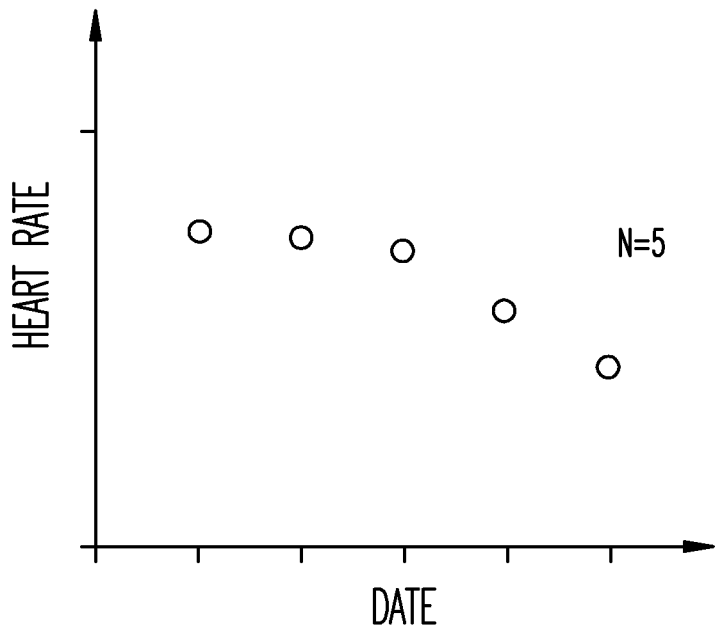
FIG. 8B depicts an exemplary appearance of the trend information of FIG. 8A.

FIG. 8A depicts yet another method of presenting trend information. Like the methods of FIGS. 6A and 7A, the method of FIG. 8A begins at 800 in which the external device receives a selection of the number of force-frequency relationships to retrieve. At 802, that particular quantity of force-frequency relationships is retrieved from the data store in which they are housed. As previously described, the time/date stamp information is retrieved at the same time, so that the corresponding date/time associated with each force-frequency relationship is known.

At 804, for each of the retrieved force-frequency relationships, the heart rate at which the curve departed substantially from linearity is determined. At 806, each departure point/heart rate calculated at 804 is presented (e.g., displayed) via the external device's output device. For example, the departure points/heart rates may be presented on a x-y chart, with departure point/heart rate measured along the y-axis, and date/time measured along the x-axis. FIG. 8B presents an example of how such a presentation may appear, assuming that five force-frequency relationships were retrieved during the execution of operation 800. (Worsening of congestive heart failure is indicated by a decline in the heart rate at which successive force-frequency relationships depart from linearity, as shown in FIG. 8B).

Figure 9:
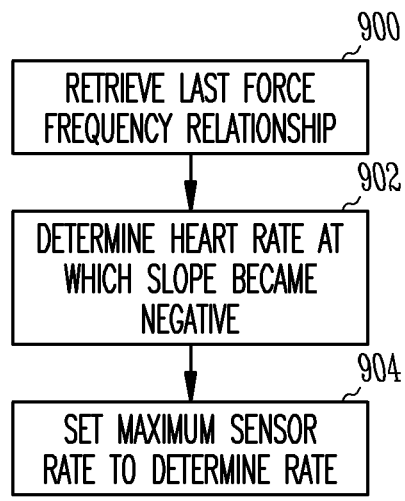
FIG. 9 depicts a method of setting a maximum sensor rate.

FIG. 9 presents a method that may be executed by a cardiac rhythm management device, or by an external device. Returning to FIG. 2, one can see that the exemplary force-frequency relationship associated with the failing heart begins to exhibit a negative slope at about 120 beats per minute. Thus, such a heart actually beats less forcefully when its rate exceeds 120 beats per minute. Therefore, a cardiac rhythm management device may respond to such information by resetting its pacing parameters to ensure that the heart does not beat at a rate in excess of 120 beats per minute.

FIG. 9 depicts a method in accord with the preceding insight. Initially, at 900, the most recent force-frequency relationship measured by the device is retrieved. At 902, the force-frequency relationship is examined to determine if at some frequency it begins to exhibit a negative slope. At 904, if such a frequency exists, the cardiac rhythm management device may be automatically or manually reprogrammed so that its maximum sensor rate is equal to the heart rate determined at 902. (The maximum sensor rate set is a pacing parameter that defines the maximum rate at which the heart will be paced in response to detected exertion of the patient.)

Figure 10:
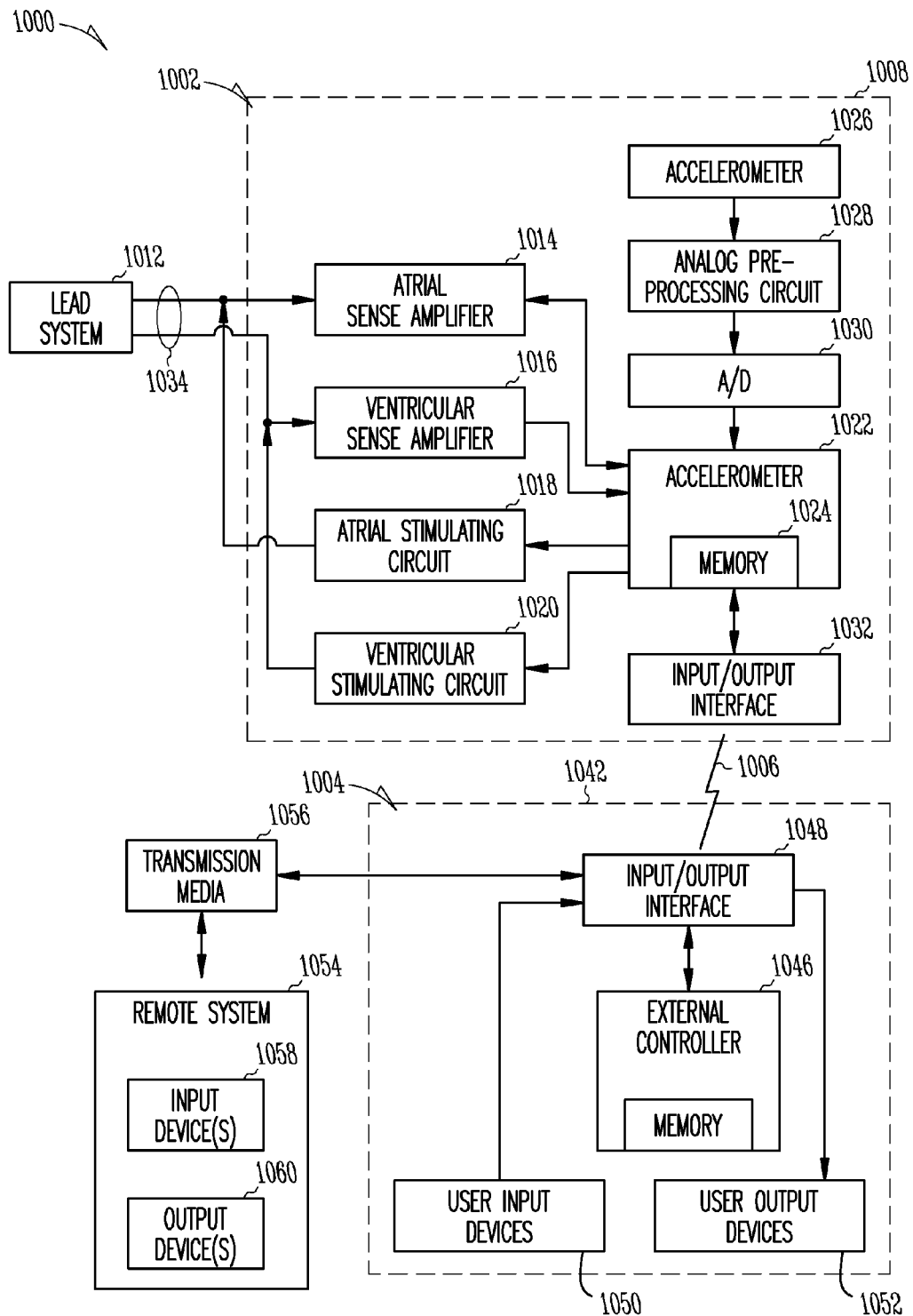
FIG. 10 depicts an exemplary cardiac rhythm management device and external device that may employ the methods and schemes presented herein.

FIG. 10 depicts an exemplary cardiac rhythm management device and external device that may employ the methods and schemes presented herein. However, these methods and schemes may also find use in other implantable or external devices.

In FIG. 10, an exemplary system 1000 for detecting and measuring force-frequency relationships includes an implantable system 1002 and an external system 1004. The implantable system 1002 and external system 1004 are configured to communicate via a communications link 1006.

The implantable system 1002 includes an implantable device 1008 typically operatively coupled to a patient's heart by a lead system 1012. The components of the implantable device 1008 typically include an atrial sense amplifier 1014, a ventricular sense amplifier 1016, an atrial stimulating circuit 1018, a ventricular stimulating circuit 1020, a controller 1022, a memory 1024, an accelerometer 1026, an analog pre-processing circuit 1028, an analog-to-digital (A/D) converter 1030, and an input/output (I/O) interface 1032. The components of implantable device 1008 are typically housed within an implantable housing (indicated by the broken lined box in FIG. 10), which may be implanted within the patient's chest cavity (e.g., in the pectoral region) or elsewhere.

The atrial sense amplifier 1014, ventricular sense amplifier 1016, atrial stimulating circuit 1018 and ventricular stimulating circuit 1020 are typically operatively coupled to the lead system 1012 via a pair of conductors 1034. The lead system 1012 may include an atrial sensing electrode and an atrial stimulating electrode adapted to be disposed in the right atrial chamber of heart and a ventricular sensing electrode and a ventricular stimulating electrode adapted to be disposed in the right ventricular chamber of the heart.

Sensed atrial and ventricular electrical signals generated by the sensing electrodes are received by the atrial and ventricular sense amplifiers 1014 and 1016, respectively. Similarly, atrial and ventricular stimulating signals generated by the atrial and ventricular stimulating circuits 1018 and 1020 are applied to the atrial and ventricular stimulating electrodes, respectively. The atrial sense amplifier 1014, ventricular sense amplifier 1016, atrial stimulating circuit 1018, and ventricular stimulating circuit 1020, are each also operatively coupled to the controller 1022.

In other embodiments, other sensing electrode configurations are used for internally sensing one or more electrical signals of the heart. In one example, only one sensing electrode may be used. Alternatively, one or more electrodes placed within the body but outside of the heart are used for sensing cardiac electrical signals. In yet another example, a sensing electrode is placed on the implantable housing. In each of these examples, the sensing electrodes are operatively coupled to the controller 1022.

In the embodiment shown in FIG. 10, the sensing electrodes and the stimulating electrodes are disposed in association with the right side of heart. In other embodiments, one or more sensing electrode(s) and one or more stimulating electrode(s) are disposed in association with the left side of the heart (in lieu of being disposed in association with the right side of the heart, or in addition to sensing electrode(s) and stimulating electrode(s) disposed in association with the right side of the heart). The addition of left heart sensing may advantageously allow for the resolution of ambiguities due to disassociation of right and left heart conduction.

The controller 1022 includes a microcontroller or microprocessor which is configured to execute a program stored in a read-only memory (ROM) portion of a memory unit 1024, and to read and write data to and from a random access memory (RAM) portion of the memory unit 1024. By executing the program stored in memory 1024, the controller 1022 is configured to process the atrial and ventricular electrical signals from the atrial and ventricular sense amplifiers 1014 and 1016, and to provide control signals to the atrial and ventricular stimulating circuits 1018 and 1020. In response, the stimulating circuits 1018 and 1020 provide stimulating pulses to the heart via atrial and ventricular stimulating electrodes at appropriate times. In other embodiments, the controller 1022 may include other types of control logic elements or circuitry.

The implantable device 1008 may be referred to as a dual-chamber pacemaker since pacemaking functions are provided to both atrial and ventricular chambers of the heart. In another embodiment, the implantable system includes a single-chamber pacemaker that senses electrical signals and provides stimulating pulses to a single chamber of the heart. In yet another embodiment, the implantable system does not provide any stimulation of heart tissues, but includes one or more sensing electrodes for sensing one or more electrical signals of the heart, and for providing corresponding sensed signals to controller 1022. In still another embodiment, the implantable system does not provide any sensing electrodes for sensing any cardiac electrical signals, but is configured to sense signals representing heart sounds using a sensor such as the accelerometer 1026, as described below and to transmit information about such heart sounds from the implantable device 1008.

In this description, the implantable device 1008 is described as a dual-chamber pacemaker for the sake of illustration. It is to be understood, however, that implantable system 1002 need not provide the stimulation functions described herein, and may provide other functions which are not described herein.

In some embodiments, a minute ventilation output channel and a minute ventilation input channel may be included. The minute ventilation output channel generates a test signal that is applied to a portion of the patient's thorax. An input channel receives and conditions a responsive signal. The content of the conditioned signal reveals respiration information.

An accelerometer 1026 may be configured to provide sensed signals to the analog pre-processing circuit 1028, which generates an analog output signal which is digitized by A/D converter 1030. The digitized accelerometer signal is received by the controller 1022. In the embodiment of FIG. 10, the accelerometer 1026 is located within the housing of implantable device 1008. In another embodiment, the accelerometer 1026 is located on the housing of the implantable device. The accelerometer 1026 may include, for example, a piezo-electric crystal accelerometer sensor of the type used by pacemakers to sense the level of physical activity of the patient, or may include other types of accelerometers. To detect heart sounds, this or other types of sound-detecting sensors or microphones may also be used, such as a pressure sensor or a vibration sensor configured to respond to sounds made by the heart. Thus, in this document, detected "heart sounds" may in fact be measured as cardiac vibrations detected by an accelerometer.

In another embodiment, the system 1000 includes two or more sound-detecting sensors. In such an embodiment, the plurality of sensed heart sound signals from the plurality of sensors may be individually transmitted to external system 1004 for display as individual traces, may be combined (e.g., averaged) by external system 1004 before being displayed as a single trace, or may be combined by controller 1022 before being transmitted to external system 1004 as a single heart sound signal. These sensors may include different types of sensors, sensors that are located in different locations, or sensors that generate sensed signals which receive different forms of signal processing.

In one embodiment, the accelerometer 1026 is configured to generate sensed signals representative of two distinct physical parameters: (1) the level of activity of the patient; and (2) the heart sounds generated by heart. Accordingly, the analog pre-processing circuit 1028 is configured to pre-process the sensed signals from the accelerometer 1026 in a manner which conforms to the signal characteristics of both of these physical parameters. For example, if the frequencies of interest for measuring the patient's level of activity are below 10 Hz, while the frequencies of interest for detecting heart sounds are between 0.05 Hz and 50 Hz, then analog pre-processing circuit 1028 may include a low-pass filter having a cutoff frequency of 50 Hz. The controller 1022 may then perform additional filtering in software. Along with filtering, analog pre-processing circuit 1028 may perform other processing functions including automatic gain control (AGC) functions.

The analog pre-processing circuit 1028, analog-to-digital converter 1030 and controller 1022 may operate together to acquire, measure, and isolate heart sounds, such as S1, S2, S3, and S4 heart sounds, as described in "METHOD AND APPARATUS FOR THIRD HEART SOUND DETECTION," U.S. application Ser. No. 10/746,853, filed Dec. 24, 2003, which is hereby incorporated by reference for all it discloses. Alternatively, the analog pre-processing circuit 1028 may simply provide automatic gain control functionality.

In some embodiments, the controller 1022 performs one or more of steps the depicted and described with reference to FIGS. 3-5. Instructions for performing the operations of the aforementioned Figures may be stored in the memory device 1024, for example. Additionally, some of the operations discussed and depicted with reference to FIG. 3-5 may be performed cooperatively by the controller 1022 within the implantable device 1008 and another controller. For example, the controller 1022 in the implantable device 1008 may perform some of the operations, communicate needed results (via communications link 1006, for example) to an external controller (contained in a programmer, for example), which may perform the remaining operations, and which may communicate results to either another external device or to the implantable device 1002.

In another embodiment, the implantable device 1008 has two pre-processing channels for receiving sensed signals from accelerometer 1026. In still another embodiment, implantable device 1008 includes two accelerometers, with one accelerometer configured to generate sensed signals representative of the level of activity of the patient and the other accelerometer configured to generate sensed signals representative of heart sounds. In these latter two embodiments, any hardware and/or software processing performed on the sensed signals can conform to the specific characteristics of the respective sensed signals. For example, the analog pre-processing circuit used for the level-of-activity sensed signals can provide a low-pass filter with a cutoff frequency of 10 Hz, while the analog preprocessing circuit for the heart-sound sensed signals can provide a band-pass filter with cutoff frequencies of 0.05 and 50 Hz. In the latter case, each accelerometer can be selected, located and/or oriented to maximize the detection of the respective physical parameter. In yet another embodiment, if the implantable device does not need to sense the level of activity of the patient, the accelerometer 1026 may measure only the sounds made by heart. In yet another embodiment, an accelerometer for sensing heart sounds may be located at the distal end of a lead. In such an embodiment, the implantable device 1002 may include an internal accelerometer (such as accelerometer 1026) for detection of the patient's motion-based activity level.

The implantable device 1002 may include or communicate with a pressure sensor that may be adapted for placement in the pulmonary artery or right ventricle, for example. Data from the pressure sensor may be relayed to the controller 1022 via an analog pre-processing circuit and analog-to-digital converter, in a manner analogous to conveyance of accelerometer data, for example. Such data may be used to determine a preload patient's preload level, as discussed with reference to known variations of the method of FIG. 3, for example.

The controller 1022 is capable of bi-directional communications with external an system 1004 via an I/O interface 1032. In one embodiment, the I/O interface 1032 communicates using RF signals, which may be understood to include inductive coupling. In other embodiments, the I/O interface 1032 communicates using optical signals, or a combination of RF and optical signals (e.g., RF signals for receiving data from the external system 1004 and optical signals for transmitting data to external system 1004, or vice-versa). The controller 1022 uses the I/O interface 1032 for bi-directional communications with the external system 1004 to support conventional monitoring, diagnostic and configuration pacemaker functions. The controller 1022 may also use the I/O interface 1032 to telemeter data representative of the heart sounds sensed by accelerometer 1026 to the external system 1004. In various embodiments, the controller 1022 further uses the I/O interface 1032 to telemeter data representative of cardiac electrical signals (i.e., electrogram or EGM signals), which may include data representative of atrial electrical signals, sensed by the atrial sensing electrode, and/or data representative of ventricular electrical signals, sensed by the ventricular sensing electrode. Thus, implantable system 1002 is capable of sensing heart sounds, atrial electrical signals and ventricular electrical signals, and of telemetering data representative of the heart sounds and/or cardiac electrical signals to external system 1004. In other embodiments, the controller 1022 telemeters data representative of cardiac electrical signals which were sensed by other configurations of internal cardiac sensing electrodes.

The external system 1004 may include an external device 1042. The external device 1042 may include an external controller 1046, an I/O interface 1048, user input device(s) 1050, and user output device(s) 1052. Using the I/O interface 1048, the external controller 1046 is configured for bi-directional communications with the implantable device 1008, for receiving input signals from input device(s) 1050, and for applying control signals to output device(s) 1052. The input device(s) 1050 include at least one input device which allows a user (e.g., a physician, nurse, medical technician, etc.) to generate input signals to control the operation of external device 1042, such as at least one user-actuatable switch, knob, keyboard, pointing device (e.g., mouse), touch-screen, voice-recognition circuit, etc. The output device(s) 1052 include at least one display device (e.g., CRT, flat-panel display, etc.), audio device (e.g., speaker, headphone), or other output device which generates user-perceivable outputs (e.g., visual displays, sounds, etc.) in response to control signals. The external controller 1046 may be configured to receive the data representative of heart sounds, atrial electrical signals and/or ventricular electrical signals from implantable system 1002, and to generate control signals that, when applied to output device(s) 1052, cause the output device(s) to generate outputs that are representative of the heart sounds, the atrial electrical signals and/or the ventricular electrical signals.

In one embodiment, the system 1000 further includes a remote system 1054 operatively coupled to communicate with the external system 1004 via transmission media 1056. The remote system 1054 includes one or more user input device(s) 1058, and one or more user output device(s) 1060, which allow a remote user to interact with remote system 1054. The transmission media 1056 includes, for example, a telephone line, electrical or optical cable, RF interface, satellite link, local area network (LAN), wide area network (WAN) such as the Internet, etc. The remote system 1054 cooperates with external system 1004 to allow a user located at a remote location to perform any of the diagnostic or monitoring functions that may be performed by a user located at external system 1004. For example, data representative of heart sounds and/or cardiac electrical signals are communicated by the external system 1004 to the remote system 1054 via the transmission media 1056 to provide a visual display and/or an audio output on the output device(s) 1060, thereby allowing a physician at the remote location to aid in the diagnosis of a patient. In various examples, the system 1054 may be located in another room, another floor, another building, another city or other geographic entity, across a body of water, at another altitude, etc., from the external system 1004.

Although not depicted in FIG. 10, the I/O interface 1032 may establish a communication link with a communication device in physical proximity to the patient. For example, the I/O interface may establish a data link with a personal digital assistant, and may upload or download any of the data mentioned previously or hereafter. The personal digital assistant may, in turn, establish a link with an access point, so that the link may be effectively extended over a network, such as the Internet.

Although the above description has emphasized the use of heart sounds to obtain contractility information, it will be understood that the force-frequency techniques described above will also be useful with other systems and devices for obtaining chronic contractility information. For example, chronic contractility information can alternatively be obtained using a chronically implanted pressure sensor, such as a left ventricular pressure sensor that is chronically implanted and attached to a chronically implanted cardiac function management or other implanted device. In another example, chronic contractility information can be obtained using a chronically implanted displacement sensor that measures heart wall movement using a transthoracic, intracardiac, or like impedance sensor signal or other such technique, and which is attached to a chronically implanted medical device, such as a pacemaker, defibrillator, cardiac resynchronization therapy, or other cardiac function management device. Using a chronically implanted medical device to obtain contractility information for determining a force-frequency relationship is useful for, among other things, tracking progression of congestive heart failure, so that an appropriate warning or therapy can be delivered.

Embodiments of the invention may be implemented in one or a combination of hardware, firmware, and software. Embodiments of the invention may also be implemented as instructions stored on a machine-readable medium, which may be read and executed by at least one processor to perform the operations described herein. A machine-readable medium may include any mechanism for storing or transmitting information in a form readable by a machine (e.g., a computer). For example, a machine-readable medium may include read-only memory (ROM), random-access memory (RAM), magnetic disc storage media, optical storage media, flash-memory devices, electrical, optical, acoustical or other form of propagated signals (e.g., carrier waves, infrared signals, digital signals, etc.), and others.

The Abstract is provided to comply with 37 C.F.R. Section 1.72(b) requiring an abstract that will allow the reader to ascertain the nature and gist of the technical disclosure. It is submitted with the understanding that it will not be used to limit or interpret the scope or meaning of the claims.

In the foregoing detailed description, various features are occasionally grouped together in a single embodiment for the purpose of streamlining the disclosure. This method of disclosure is not to be interpreted as reflecting an intention that the claimed embodiments of the subject matter require more features than are expressly recited in each claim. Rather, as the following claims reflect, inventive subject matter lies in less than all features of a single disclosed embodiment. Thus, the following claims are hereby incorporated into the detailed description, with each claim standing on its own as a separate preferred embodiment.

What is claimed is:

1. A system comprising:
   a transducer configured to measure a heart sound characteristic of a heart;
   a control circuit configured to:
      receive the heart sound characteristic;
      determine a contractility characteristic of the heart using the measured heart sound characteristic;
      determine a corresponding heart rate indicating how frequently the heart is contracting;
      alter a pacing rate to determine and store in a memory device a group of (contractility characteristic, heart rate) pairs over a range of heart rates, the group of pairs over the range of heart rates defining a force-frequency relationship for the heart; and
      determine a slope for at least some of the group of (contractility characteristic, heart rate) pairs based, at least in part, on at least one of a linear regression and a curve fit performed on the at least some of the group of (contractility characteristic, heart rate) pairs;
   a stimulating circuit coupled to the control circuit, the stimulating circuit configured to deliver, in response to a control signal from the control circuit upon the control circuit determining the slope, stimulating signals based, at least in part, on the previously determined slope for the at least some of the group of (contractility characteristic, heart rate) pairs.

2. The system of claim 1, wherein the control circuit is configured to alter the pacing rate from a first pacing rate to a second pacing rate.

3. The system of claim 1, wherein the force-frequency relationship includes a trend of contractility characteristics and heart rates corresponding to the respective contractility characteristics.

4. The system of claim 1, wherein the control circuit is configured to provide an indication of a cardiac status of the heart using the force-frequency relationship.

5. The system of claim 4, wherein the control circuit is configured to provide an indication of congestive heart failure status of the heart using the force-frequency relationship.

6. The system of claim 1, including an implantable medical device, and wherein the implantable medical device includes the transducer and the control circuit.

7. The system of claim 1, wherein the stimulating circuit is configured to deliver the stimulating signals at a heart rate corresponding to the slope being negative.

8. An implantable medical device comprising:
   a control circuit configured to:
      receive a heart sound characteristic of a heart;
      determine a heart rate corresponding to the heart sound characteristic, the heart rate indicating how frequently the heart is contracting;
      determine a first (contractility characteristic, heart rate) pair at a first pacing rate;
      determine a second (contractility characteristic, heart rate) pair at a second pacing rate, the second pacing rate different than the first pacing rate;
      store the first and second pairs in a memory device, the first and second pairs each defining a force-frequency relationship of the heart; and
      determine a slope for the first and second (contractility characteristic, heart rate) pairs based, at least in part, on at least one of a linear regression and a curve fit performed on the first and second (contractility characteristic, heart rate) pairs;
   a stimulating circuit coupled to the control circuit, the stimulating circuit configured to deliver, in response to a control signal from the control circuit upon the control circuit determining the slope, stimulating signals based, at least in part, on the previously determined slope for at least some of the first and second (contractility characteristic, heart rate) pairs.

9. The implantable medical device of claim 8, including a transducer configured to measure the heart sound characteristic.

10. The implantable medical device of claim 9, wherein the heart sound information is indicative of left ventricular pressure of the heart; and
    wherein the control circuit is configured to alter the pacing rate over a range of heart rates including the first pacing rate and the second pacing rate to determine a group of (contractility characteristic, heart rate) pairs, wherein the slope is based, at least in part, on the group of (contractility characteristic, heart rate) pairs.

11. The implantable medical device of claim 8, wherein the control circuit is configured to provide an indication of congestive heart failure status of the heart using the slope.

12. The implantable medical device of claim 8, wherein the stimulating circuit is configured to deliver the stimulating signals at a heart rate corresponding to the slope being negative.

13. A method comprising:
    receiving a heart sound characteristic of a heart;
    determining a corresponding heart rate indicating how frequently the heart is contracting based, at least in part, on the heart sound characteristic;
    determining a first (contractility characteristic, heart rate) pair at a first pacing rate;
    determining a second (contractility characteristic, heart rate) pair at a second pacing rate;
    store the first and second pairs in a memory device, the first and second pairs each defining a force-frequency relationship of the heart;
    determining a slope for the first and second (contractility characteristic, heart rate) pairs based, at least in part, on at least one of a linear regression and a curve fit performed on the first and second (contractility characteristic, heart rate) pairs; and
    delivering stimulating signals to the heart based, at least in part, on the previously determined slope.

14. The method of claim 13, including altering the pacing rate from the first pacing rate to the second pacing rate.

15. The method of claim 13, wherein determining the slope includes providing a trend of contractility characteristics and heart rates corresponding to the respective contractility characteristics.

16. The method of claim 13, wherein determining the slope includes providing an indication of a cardiac status of the heart using the first and second contractility characteristics and the first and second pacing rates.

17. The method of claim 16, wherein the providing the indication of cardiac status of the heart includes providing an indication of congestive heart failure of the heart.

18. The method of claim 13, wherein the receiving the heart sound characteristic includes implantably receiving the heart sound characteristic.

19. The method of claim 13, wherein receiving the heart sound characteristic further includes receiving via an implantable device a left ventricular pressure information.

20. The method of claim 13, wherein the stimulating signals are delivered to the heart at a heart rate corresponding to the slope being negative.

21. A system comprising:
   an accelerometer configured to receive heart contraction information of a heart and to produce a contractility signal;
   a control circuit configured to:
      receive the contractility signal;
      determine a first contractility characteristic of the heart using the contractility signal;
      determine a corresponding heart rate indicating how frequently the heart is contracting; and
      alter a pacing rate to determine and store in a memory device a group of (contractility characteristic, heart rate) pairs over a range of heart rates, the group of pairs over the range of heart rates defining a force-frequency relationship for the heart; and
      determine a slope for at least some of the group of (contractility characteristic, heart rate) pairs based, at least in part, on at least one of a linear regression and a curve fit performed on the at least some of the group of (contractility characteristic, heart rate) pairs;
   a stimulating circuit coupled to the control circuit, the stimulating circuit configured to deliver, in response to a control signal from the control circuit upon the control circuit determining the slope, stimulating signals based, at least in part, on the previously determined slope for the at least some of the group of (contractility characteristic, heart rate) pairs.

22. The system of claim 21, wherein the stimulating circuit is configured to deliver simulating signals based on the pacing rate, and wherein the stimulating circuit is configured to alter delivery of the stimulating signals from a first pacing rate to a second pacing based, at least in part, on a control from the control circuit.

23. The system of claim 21, wherein the slope includes a trend of contractility characteristics and heart rates corresponding to the respective contractility characteristics.

24. The system of claim 21, wherein the control circuit is configured to provide an indication of a cardiac status of the heart using the slope.

25. The system of claim 24, wherein the control circuit is configured to provide an indication of congestive heart failure status of the heart using the slope.

26. The system of claim 21, including an implantable medical device, and wherein the implantable medical device includes the accelerometer and the control circuit.

27. The system of claim 21, wherein the heart contraction information includes at least one of left ventricular pressure information or heart sound information, and wherein the contractility signal includes at least one of a left ventricular pressure signal or a heart sound signal.

28. The system of claim 21, wherein the stimulating circuit is configured to deliver the stimulating signals at a heart rate corresponding to the slope being negative.

29. The system of claim 21, further comprising a lead, wherein the accelerometer is positioned on the lead.

* * * * *